United States Patent
Schampers et al.

(10) Patent No.: US 8,921,785 B2
(45) Date of Patent: Dec. 30, 2014

(54) COOPERATING CAPILLARY AND CAP FOR USE IN A HIGH-PRESSURE FREEZER

(71) Applicant: FEI Company, Hillsboro, OR (US)

(72) Inventors: Rudolf Johannes Perer Gerardus Schampers, Tegelen (NL); Johannes Antonius Hendricus W. G. Persoon, Waalre (NL); Andreas Theodorus Engelen, Eindhoven (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/021,703

(22) Filed: Sep. 9, 2013

(65) Prior Publication Data

US 2014/0072964 A1    Mar. 13, 2014

Related U.S. Application Data

(60) Provisional application No. 61/699,334, filed on Sep. 11, 2012.

(30) Foreign Application Priority Data

Sep. 11, 2012    (EP) ..................... 12183821

(51) Int. Cl.
H01J 37/26    (2006.01)
(52) U.S. Cl.
USPC ...... 250/311; 250/306; 250/307; 250/440.11; 250/288
(58) Field of Classification Search
USPC ......... 250/281, 282, 288, 306, 307, 309, 310, 250/311, 440.11
See application file for complete search history.

(56) References Cited

U.S. PATENT DOCUMENTS

| 5,270,552 | A | 12/1993 | Ohnishi et al. |
| 6,758,362 | B2 | 7/2004 | Studer |
| 2006/0014134 | A1* | 1/2006 | Fuhr et al. .......................... 435/2 |
| 2006/0053807 | A1* | 3/2006 | Gerhardt et al. .................. 62/80 |
| 2013/0260452 | A1* | 10/2013 | Toner et al. ................ 435/307.1 |

FOREIGN PATENT DOCUMENTS

| EP | 2009421 | 12/2008 |
| WO | 2012038484 | 3/2012 |

OTHER PUBLICATIONS

Lich, Ben, "Site Specific Three-dimensional Structural Analysis in Tissues and Cells Using Automated DualBeam Slice and View," Microscopy Today, Mar. 2007, pp. 26-30.

* cited by examiner

*Primary Examiner* — Nicole Ippolito
(74) *Attorney, Agent, or Firm* — Scheinberg & Associates, PC; Michael O. Scheinberg; John B. Kelly

(57) ABSTRACT

The invention relates to an assembly of a cooperating capillary and cap for containing an aqueous solution in an inner volume of the capillary. The assembly is used in a high pressure freezer in which the aqueous solution is frozen at a high pressure to form an amorphous frozen sample at a cryogenic temperature. The cap forms a closure at one end of the capillary, and the part of the cap that is in contact with the inner volume of the capillary has an indent; as a result of which the cap, after freezing the aqueous solution, can be removed from the capillary and a free standing pillar of frozen aqueous material extends from the capillary.

15 Claims, 3 Drawing Sheets

COOPERATING CAPILLARY AND CAP FOR USE IN A HIGH-PRESSURE FREEZER

Figure 1A:
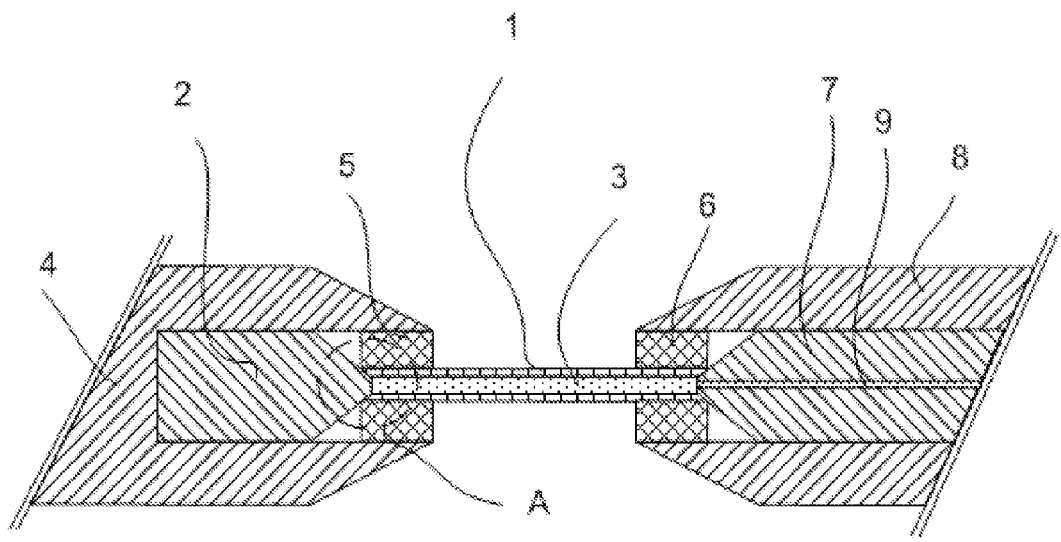

This Application claims priority from U.S. Provisional Application 61/699,334, filed Sep. 11, 2012, which is hereby incorporated by reference.

The invention relates to an assembly of cooperating capillary and cap for containing an aqueous solution in an inner volume of the capillary, the assembly equipped to be used in a high pressure freezer in which the aqueous solution is frozen at a high pressure to form an amorphous frozen sample at a cryogenic temperature, the inner volume of the capillary having a diameter of less than 500 µm, preferably less than 350 µm, and the cap equipped to form a closure to one end of the capillary.

The invention further relates to a method for using such an assembly.

Such an assembly is known from, for example, U.S. Pat. No. 6,758,362 to Leica AG.

High pressure freezing (HPF) is a technique used to form samples with amorphous ice. It is known that such samples can be formed by rapidly cooling a thin sample, but a cooling rate in excess of $10^4$ K/s must be used as otherwise ice crystals may form. It is known that a lower cooling rate can be used provided that the sample is pressurized. At a pressure of approximately 2100 bar a cooling rate of, for example, $10^3$ K/s results in an amorphous (vitrified) sample. Due to this lower cooling rate thicker samples can be formed. Also the success rate (percentage of samples that are free of ice crystals) may be increased.

It is noted that amorphous ice is stable at a temperature below the glass transition temperature of water, which is approximately 135 K.

The known patent to Leica AG describes the use of a metal capillary that is loaded with an aqueous solution comprising sample material. Typically the metal capillary has an outer diameter of 650 µm and an inner diameter of 350 µm (derived from the "Operating manual specimen tube system" for LEICA EM PACT2). The aqueous solution is contained in a still smaller capillary made of, for example, cellulose or a polymer, that fits within the metal capillary. If a cellulose capillary is used it is preferably surrounded by a thin layer of a non water-miscible fluid, such as a hydrocarbon with a low freezing point (preferably less than −120° C.), for example 1-pentene, 1-chlorobutane, or the like. Preferably the metal capillary shows two ends, each showing a conical indent or conical recess. One end of the capillary is closed by a cap ending in a cone, the top of the cone fitting and centering in the recess of the capillary. The other end of the capillary is connected to a high pressure tube via a steel tube with a conical end, the end fitting in the recess of the capillary. The tube connects the capillary in working to a high pressure fluid, such as oil, to pressurize the aqueous solution within the capillary to a pressure of preferably 2100 bar.

The sample is vitrified by pressurizing it to approximately 2100 bar and quickly cooling it to a temperature below the glass transition temperature, after which the sample is depressurized. As the sample is surrounded by a liquid, the whole cellulose inner capillary can then be extruded by pushing it out of the metal capillary with, for example, a wire or drill bit of appropriate diameter.

A disadvantage of this method is that a large part of the already small volume of the metal capillary is filled with non-sample material: not only the cellulose of polymer capillary, but also the non-water miscible material is present in the metal capillary with an inner diameter of only 350 µm.

It is noted that it is also known to fill the metal capillary completely with sample material, and work without the cellulose capillaries. In that case the metal capillary must be opened after freezing the sample, for example by shaving it with a microtome.

A disadvantage of this method is that the exposed sample material may be deformed due to the forces exerted thereon when removing the metal (when opening the capillary).

In yet another method the metal is removed with an ion beam using a Focused Ion Beam machine or a machine equipped with both an electron beam column and an ion beam column. This has the advantage that the sample can be inspected with the electron beam column and the sample can be machined with the ion beam column for forming a block face or a lamella. However, a disadvantage is that the milling rate of metal is relatively low, and that it thus takes long to expose sample material.

There is a demand for a method offering higher throughput, without deformation. The invention intends to offer such a method.

To that end the part of the cap that is in contact with the inner volume of the capillary when the cap forms a closure, shows an indent, as a result of which the cap, after freezing the aqueous solution, can be removed from the capillary and a free standing pillar of frozen aqueous material extends from the capillary.

By forming the cap such that sample material extends in an indent (preferably a conical recess), inventors found that, when the sample was frozen, the cap could be removed leaving a part of the sample material exposed and accessible to further inspection.

It is noted that freeing the sample and forming, for example, block faces and/or lamella must be done at a temperature below the glass transition temperature, as otherwise (re)crystallization occurs. Therefore the sample must be kept at a temperature of approximately −130° C. or less from the moment of freezing until it is inspected, or treated such that it can be thawed (for example by freeze-substitution).

This is true for a method using the prior are cap-and-capillary as well as for the method using the cooperating cap-and-capillary according to the invention.

Preferably the capillary is a metal capillary, more specifically steel or copper. The cap should show a high thermal conductivity and a low thermal capacity, enabling fast cooling of the material in the indent, and should thus preferably be made of a metal or a ceramic material.

It is noted that to avoid that sample material in the cap is broken from the sample material in the capillary and stays in the cap when removing the cap, the depth of the indent is preferably half the diameter of the capillary or less. In the case of a cone the resultant top angle is thus 90° or more. Furthermore the cone is preferably blunted, lacking a sharp top.

In an aspect of the invention a method of inspecting a cryogenic sample, the method comprising:

Providing sample material in an assembly of a cooperating capillary and cap
Inserting the assembly in a high pressure freezer,
Form an amorphous cryogenic sample,
Remove the cap from the capillary,
Inspecting the frozen sample material at a cryogenic temperature Is Characterized in that
The cap is a cap with an indent, and
When removing the cap a free standing pillar of sample material is exposed.

The inspection may be the inspection of a block face, or the inspection of lamella (thin slices).

In an embodiment the inspection comprises the inspection with a charged particle beam.

This embodiment describes inspecting the sample with an electron beam, an ion beam, or a charged cluster beam. As known to the person skilled in the art an electron beam offers a very high resolution (from 1 nm at 200 eV using a Scanning Electron Microscope (SEM) to 0.05 nm at 300 keV using a TEM)

In another embodiment the surface of the block face or the lamella is machined with an ion beam.

Forming the surface to be inspected by machining the sample with a focused ion beam results in a smooth surface without exerting pressure to the sample, and also enables the fabrication of very thin lamella as needed in hi-resolution Transmission Electron Microscopy (TEM).

By thus machining the sample inside the charged particle apparatus, a block-face or lamella can be made and inspected, after which a slice can be removed and another block-face or lamella can be inspected. This is known as Slice&View, and is described in, for example, "Site Specific Three-dimensional Structural Analysis in Tissues and Cells Using Automated DualBeam Slice&View", B. Lich, Microscopy Today, March 2007, pp 26-30, further referred to as Lich [-1-]. As the sample need not be taken outside of the capillary, no shearing of the capillary is needed (which may result in deformation of the sample material) and also no metal needs to be removed (thus resulting in a higher throughput). It is noted that the combination of completely in-situ Slice&View working also results in faster work method.

In yet another embodiment the lamella is inspected after freeze substitution.

Freeze substitution offers the possibility to exchange the water in the sample to other materials, resulting in a so-called fixed sample that can be inspected at room temperature. Such a process is described in, for example, International Application Publication WO 2012/038484 to the University of Utrecht Holding BV.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the invention as set forth in the appended claims.

For a more thorough understanding of the present invention, and advantages thereof, the invention is explained using figures, in which identical reference numerals indicate corresponding features.

Figure 1B:
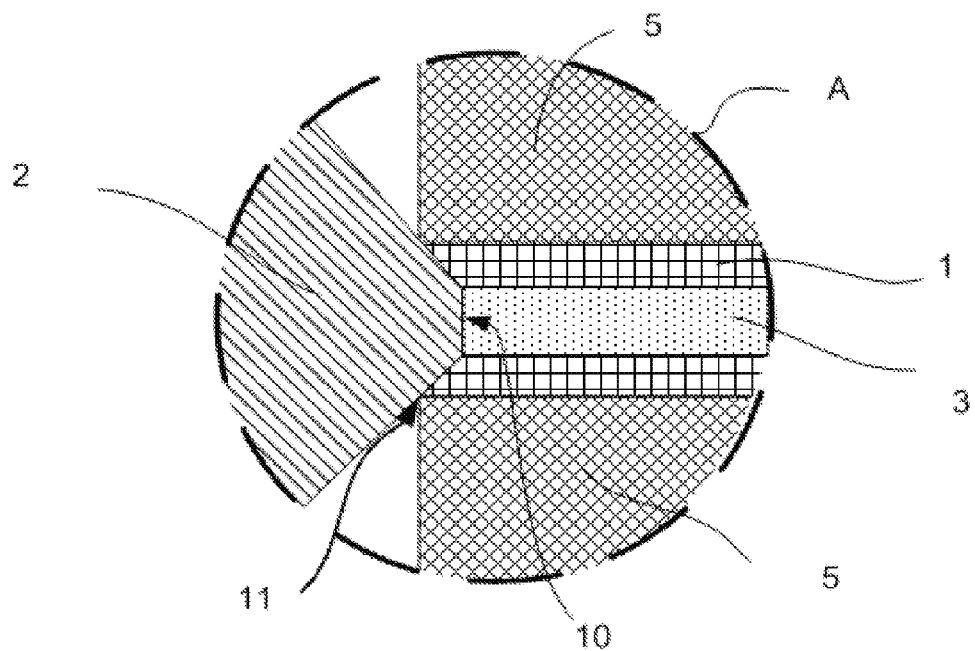
Figure 2A:
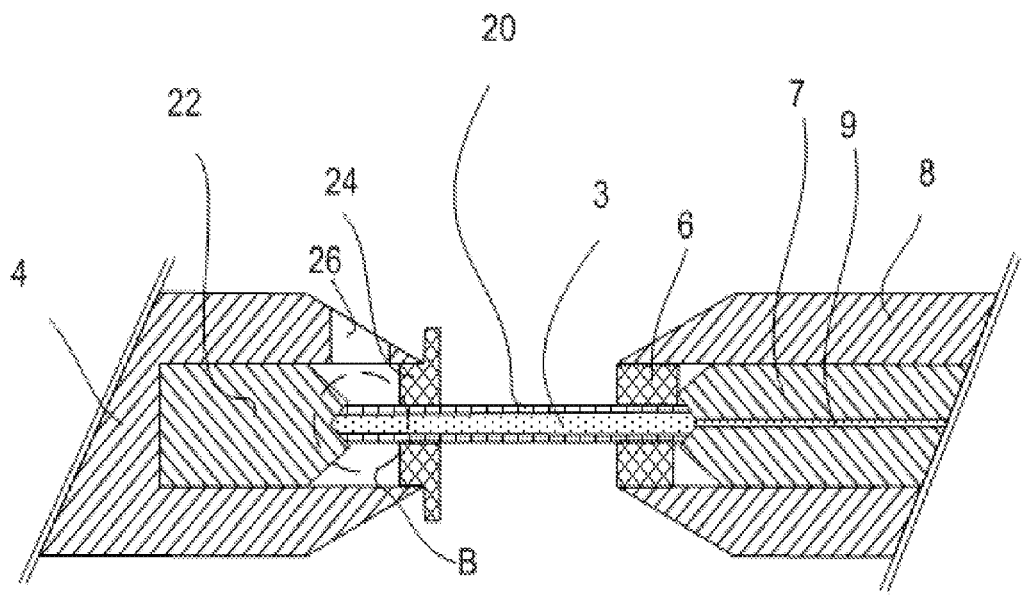
Figure 2B:
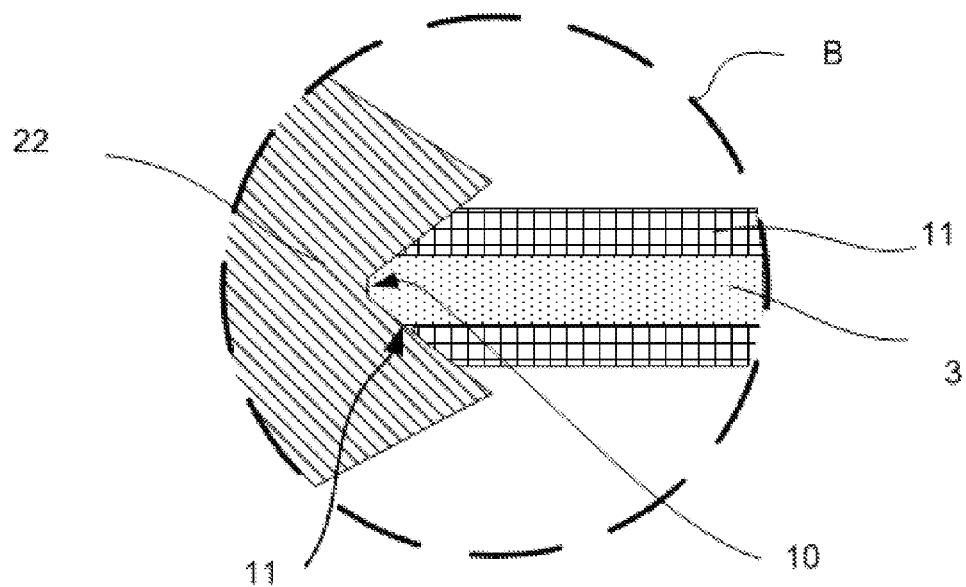
Figure 3:
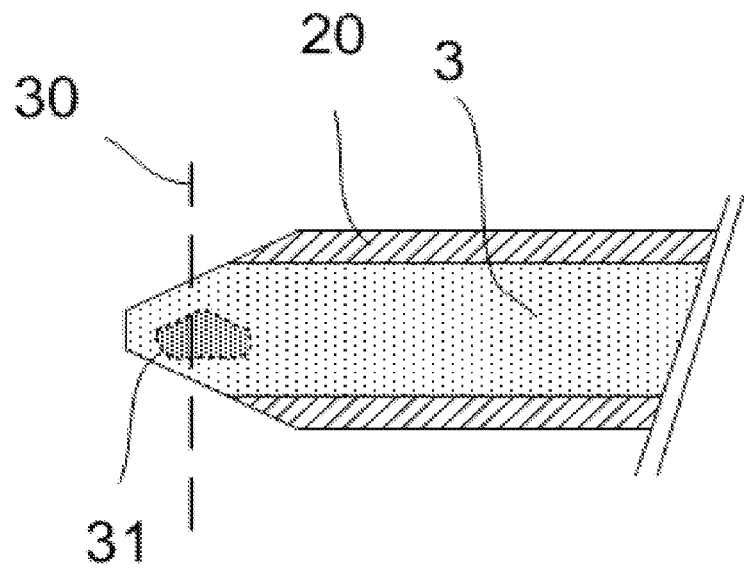

To that end:

FIG. 1A schematically shows a prior art cap-and-capillary;

FIG. 1B schematically shows a detail of FIG. 1A;

FIG. 2A schematically shows a cap-and-capillary according to the invention;

FIG. 2B schematically shows a detail of FIG. 2A;

FIG. 3 schematically shows the capillary after removal of the cap.

Figure 4:
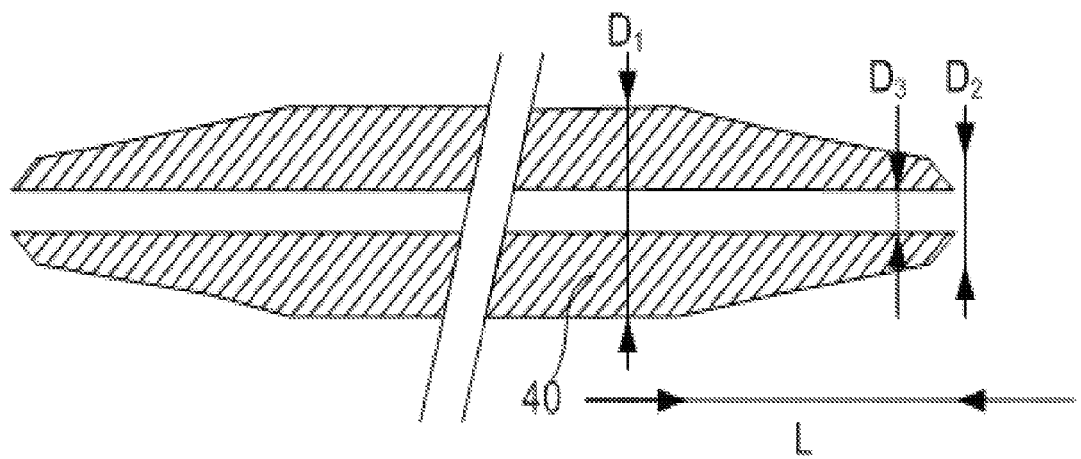

FIG. 4 shows an alternative capillary according to the invention.

FIG. 1A schematically shows a prior art cap-and-capillary;

FIG. 1A shows a capillary 1 that is filled with aqueous sample material 3. On the left side the capillary is closed at one end with a cap 2, forming a seal with the capillary. The cap fits in a holder 4, while a ferrule 5 keeps the capillary centered. On the right side a ferrule 6 keeps the capillary centered, and a cap 7 is held in a holder 8. Cap 7 shows an axial channel 9 for feeding hydraulic fluid to the inside of the capillary, thereby pressurizing the inside of the capillary, and thus the sample material 3.

It is noted that the holder 4 and holder 8 are connected to each other before inserting it in the high-pressure freezer.

It is noted that the main function of ferrules 5 and 6 is to avoid bending out of the capillary when the caps 2 and 7 are pressed against the capillary.

The capillary is first filled with the sample material, for example a solution comprising cells or cell fragments, proteins, viruses, etc. Then the capillary is inserted in the holder, the caps are pressed to the capillary to form a seal and the holder with the capillary and caps is inserted in the high-pressure freezer. The pressure is increased to approximately 2100 bar by means of the hydraulic fluid in channel 9 and a cryogenic fluid is blown against the capillary. As a result the temperature of the capillary and its contents is quickly lowered and the aqueous solution is turned in an amorphous frozen material. In this context amorphous means without observable ice crystals. While keeping the capillary and its contents at a cryogenic temperature (below the glass transition temperature) the capillary is then depressurized and taken out of the holders 4 and 8. The capillary is then cut or shaved open, after which the sample material (cells or cell fragments, proteins, viruses, etc.) becomes exposed.

It is noted that, to avoid crystallization and also the avoid condensation of ice on the capillary, the handling is preferably done in a bath of a cryogenic fluid, such as liquid nitrogen.

Exposing the sample material by cutting and exposing it by shaving the capillary often implies deformation of the capillary and its frozen contents. Even the use of a microtome or an ultramicrotome does not prevent this.

It is noted that first of all the sample material close to the distal end of the capillary where cap 2 fits in the capillary is likely to show ice crystals, as the ferrule prevents the cooling liquid to come in good thermal contact with the capillary, especially as there is no easy path to enter the volume 10.

Cut-out A is shown in more detail in FIG. 1B.

FIG. 1B shows detail A of FIG. 1A.

FIG. 1B shows a cap 2 closing capillary 1. The capillary contains sample material 3, either liquid (before freezing) or as an amorphous frozen sample (after high-pressure freezing). Furthermore ferrule 5 is shown, the ferrule necessary to avoid the capillary bending outwards.

Attention is drawn to the face 11 that is the most protruding part of the capillary, and face 12 that is the protruding part of the frozen material. Clearly no part of the sample material extends from the capillary, and even when the sample material in this extremity of the capillary should be well frozen (amorphous)—which is unlikely due to aforementioned reasons—easy inspection of the sample material is impossible.

FIG. 2A schematically shows a cap-and-capillary according to the invention.

FIG. 2A can be thought to be derived from FIG. 1A. but differs from FIG. 1A in that:

Ferrule 25 is different from ferrule 5 to enable cooling liquid to blow against the end of the capillary;

Holder 24 differs from holder 4 in that it is perforated with several holes (hole 26 shown) to direct the cooling liquid to the capillary;

Cap 22 differs from cap 2 in that it contains an indent;

Capillary 20 has a sharp needle end fitting in the indent of cap 22.

It is noted that in this figure both ends of the capillary are sharp tipped and the other cap, cap 7, also shows an indent, this to avoid that the capillary is loaded wrong.

Detail B is shown in more detail in FIG. 2B.

FIG. 2B shows detail B shown in FIG. 2A.

The differences are already discussed. As plane 10 now extends from the capillary, frozen material is left exposed (outstanding) when removing the cap.

FIG. 3 shows the capillary after removal of the cap. Clearly visible a part of the sample is left exposed, including an (encapsulated) cell 31. After machining the frozen sample with an ion beam along plane 30 a block-face is left to be inspected with, for example, an electron beam, an X-ray beam, or the like. Alternatively lamella can be formed and inspected, the lamella either connected to the bulk as described in Lich [-1-], or mounted to a manipulator and lifted out of the bulk as described in, for example, U.S. Pat. No. 5,270,552 to Hitachi.

It is noted that the block-face or the lamella can be formed without using the ion beam to remove metal, resulting in a high average mill rate FIG. 4 shows an alternative capillary according to the invention.

For optimum quality near the end of the capillary, the cooling fluid used by the high-pressure freezer should have free access to said extremity. The ferrule 24 used in FIG. 2, even when perforated, hampers free access. Therefore a way was found in which said specifically ferrule 24 can be deleted, without having an enlarged chance that the capillary would bend-out. To that end a large part 40 of the capillary is formed with a thicker wall, making that part thereby stiffer and less susceptible to bending out.

As the capillary is preferably symmetric, the sample also holds for ferrule 6.

Successful experiments were done with a copper capillary closely resembling the drawing shown in FIG. 4, in which D1 was 3 mm, D2 was 0.65 mm and D3 was 0.3 mm. L was approximately 18 mm.

It is noted that, due to the thicker wall, the freezing within the part of the capillary with the thicker wall may have occurred slower, resulting in ice crystals. However, as this part is not inspected anyway, crystallization in the part with a thick wall is not seen as a problem.

PATENT LITERATURE

[-1-] "Site Specific Three-dimensional Structural Analysis in Tissues and Cells Using Automated DualBeam Slice &View", B. Lich, Microscopy Today, March 2007, pp 26-30.

We claim as follows:

1. An assembly of cooperating capillary and cap for containing an aqueous solution in an inner volume of the capillary, the assembly being used in a high pressure freezer in which the aqueous solution is frozen at a high pressure to form an amorphous frozen sample at a cryogenic temperature, the inner volume of the capillary having a diameter of less than 500 µm, preferably less than 350 µm, and the cap forming a closure to one end of the capillary; wherein the part of the cap that is in contact with the inner volume of the capillary when the cap forms a closure, shows an indent, and the capillary has a sharp needle end fitting in the indent of the cap, as a result of which the cap, after freezing the aqueous solution, can be removed from the capillary and a free standing pillar of frozen aqueous material extends from the capillary.

2. The assembly of claim 1 in which the indent takes the form of a conical indent or a truncated conical indent and the free standing pillar takes the form of a cone or a truncated cone.

3. The assembly of claim 1 in which the indent has a diameter larger than its depth.

4. The assembly of claim 1 in which the capillary is a metal capillary.

5. The assembly of claim 1 in which the cap is a metal cap or a ceramic cap.

6. The assembly of claim 1 in which the wall thickness of the capillary in the middle is thicker than at least the end of the capillary that forms a closure with the cap.

7. A method of inspecting a cryogenic sample, the method comprising:
   providing sample material in an assembly of a cooperating capillary and cap;
   inserting the assembly in a high pressure freezer;
   forming an amorphous cryogenic sample;
   removing the cap from the capillary; and
   inspecting the frozen sample material at a cryogenic temperature;
   wherein:
   the cap is a cap with an indent;
   capillary has a sharp needle end formed to fit in the indent of the cap; and
   when removing the cap a free standing pillar of sample material is exposed.

8. The method of claim 7 in which the sample material is inspected in the sample chamber of a charged particle beam and the surface of the sample material is machined with a focused ion beam to form a block face or a lamella.

9. The method of claim 8 in which the cap is removed from the capillary in the sample chamber.

10. The method of claim 7 in which the sample is a lamella and the sample is inspected after freeze substitution.

11. The method of claim 7 in which the indent takes the form of a conical indent or a truncated conical indent and the free standing pillar takes the form of a cone or a truncated cone.

12. The method of claim 7 in which the indent has a diameter larger than its depth.

13. The method of claim 7 in which in which the capillary is a metal capillary.

14. The method of claim 7 in which the cap is a metal cap or a ceramic cap.

15. The method of claim 7 in which the wall thickness of the capillary in the middle is thicker than at least the end of the capillary that forms a closure with the cap.

* * * * *